(12) United States Patent
Chen et al.

(10) Patent No.: US 12,165,772 B2
(45) Date of Patent: Dec. 10, 2024

(54) ENTITY RELATION MINING METHOD BASED ON BIOMEDICAL LITERATURE

(71) Applicant: ZHEJIANG UNIVERSITY, Zhejiang (CN)

(72) Inventors: Ming Chen, Hangzhou (CN); Qi Chen, Hangzhou (CN); Yincong Zhou, Hangzhou (CN); Dahui Hu, Hangzhou (CN); Wenyi Wu, Hangzhou (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 231 days.

(21) Appl. No.: 17/780,649

(22) PCT Filed: Feb. 25, 2021

(86) PCT No.: PCT/CN2021/077892
§ 371 (c)(1),
(2) Date: May 27, 2022

(87) PCT Pub. No.: WO2021/190236
PCT Pub. Date: Sep. 30, 2021

(65) Prior Publication Data
US 2023/0007965 A1   Jan. 12, 2023

(30) Foreign Application Priority Data
Mar. 23, 2020   (CN) .......................... 202010208715.1

(51) Int. Cl.
*G06F 16/248*   (2019.01)
*G06F 40/295*   (2020.01)
*G16H 50/70*   (2018.01)

(52) U.S. Cl.
CPC .......... *G16H 50/70* (2018.01); *G06F 40/295* (2020.01)

(58) Field of Classification Search
CPC ...... G06F 16/248; G06F 16/355; G06F 17/18; G06F 40/30; G06F 16/285; G06F 40/295;
(Continued)

(56) References Cited

U.S. PATENT DOCUMENTS 9,965,726 B1 *   5/2018   Tablan .................. G06N 20/00
10,957,433 B2 *   3/2021   Lucas .................. G16H 70/00
(Continued)

FOREIGN PATENT DOCUMENTS

CN   107609163 A   1/2018
CN   109446338 A   3/2019
(Continued)

OTHER PUBLICATIONS

Lee et al., Deep learning of mutation-gene-drug relations from the literature, 2018, BMC Bioinformatics, pp. 1-12 (Year: 2018).*
(Continued)

*Primary Examiner* — Jakieda R Jackson
(74) *Attorney, Agent, or Firm* — KDW Firm PLLC

(57) ABSTRACT

The present disclosure provides an entity relation mining method based on a biomedical literature, including the following steps: querying a disease-associated biomedical literature in a public database, and performing data preprocessing to obtain biomedical text data; performing biomedical named entity recognition on obtained biomedical text data in combination with a regex matching pattern and a deep learning model; and mining an entity relation with transfer learning and reinforcement learning based on an entity recognition result. By acquiring the disease-associated biomedical literature from a network, extracting an abstract and a title and performing entity recognition and relation mining, the present disclosure can effectively recognize biomedical noun entities in the literature and mine potential relations between various entities.

7 Claims, 4 Drawing Sheets

(58) Field of Classification Search
CPC .......... G06F 18/24; G06F 18/23; G06F 16/35; G06N 20/00; G06N 5/022; G06N 5/04; G06N 3/044; G16B 50/10; G16H 50/70; G16H 70/60; G16H 50/20; G10L 15/16; G10L 25/30; G10L 15/22; G10L 16/063

See application file for complete search history.

(56) References Cited

U.S. PATENT DOCUMENTS

| | | | | |
|---|---|---|---|---|
| 11,971,963 | B2* | 4/2024 | Eser | G06F 18/214 |
| 2006/0064415 | A1* | 3/2006 | Guyon | G16B 40/10 |
| 2009/0019032 | A1* | 1/2009 | Bundschus | G16H 50/70 |
| | | | | 707/999.005 |
| 2013/0262091 | A1* | 10/2013 | Zhang | G06F 40/40 |
| | | | | 704/9 |
| 2015/0370782 | A1* | 12/2015 | Fan | G06F 40/30 |
| | | | | 704/9 |
| 2016/0140234 | A1* | 5/2016 | Van Den Broek | H04L 67/10 |
| | | | | 707/706 |
| 2016/0232455 | A1* | 8/2016 | Carus | G06F 40/216 |
| 2017/0286390 | A1* | 10/2017 | Yashpe | G06F 40/253 |
| 2018/0218253 | A1* | 8/2018 | Sen | G06N 20/10 |
| 2019/0005395 | A1* | 1/2019 | Dutkowski | G06T 11/206 |
| 2019/0065467 | A1* | 2/2019 | Dey | G06F 40/295 |
| 2019/0236153 | A1* | 8/2019 | Elliott | G06F 16/313 |
| 2019/0236492 | A1* | 8/2019 | Saha | G06F 40/295 |
| 2019/0370616 | A1* | 12/2019 | Eser | G06F 18/21355 |
| 2020/0019859 | A1* | 1/2020 | Kyriazopoulou Panagiotopoulou | G06N 20/20 |
| 2020/0065374 | A1* | 2/2020 | Gao | G06N 3/08 |
| 2021/0090694 | A1* | 3/2021 | Colley | G16H 15/00 |

FOREIGN PATENT DOCUMENTS

| | | |
|---|---|---|
| CN | 109710763 A | 5/2019 |
| CN | 109871538 A | 6/2019 |
| CN | 111428036 A | 7/2020 |

OTHER PUBLICATIONS

Tong et al., Using deep neural network to recognize mutation entities in biomedical literature, 2018, IEEE, pp. 2329-2332.*
International Search Report issued Jun. 4, 2021 for International Patent Application No. PCT/CN2021/077892.

* cited by examiner

ENTITY RELATION MINING METHOD BASED ON BIOMEDICAL LITERATURE

CROSS REFERENCE TO RELATED APPLICATION

The present application is a § 371 national phase application of Intl. Appln. No. PCT/CN2021/077892, which claims priority to the Chinese Patent Application No. 202010208715.1, filed with the China National Intellectual Property Administration (CNIPA) on Mar. 23, 2020, and entitled "ENTITY RELATION MINING METHOD BASED ON BIOMEDICAL LITERATURE", each of which is incorporated herein by reference in its entirety.

TECHNICAL FIELD

The present disclosure relates to the technical field of text data mining, and in particular, to an entity relation mining method based on a biomedical literature.

BACKGROUND ART

With the rapid development of biomedical technologies, the number of biomedical literatures is experiencing an unprecedented and explosive growth. It is an arduous task for biomedical researchers to acquire effective information from massive literature databases. Non-coding RNAs (ncRNAs) and protein-coding genes are important objects to research diseases. According to research findings, potential relations of genes, ncRNAs, proteins and so on with the diseases are helpful for biologists to explore secrets for life origin, health maintenance and disease treatment more effectively. At present, most databases mined and constructed from the biomedical literature are manually compiled by domain experts. However, in the face of the exponentially growing literature, the manual collection is greatly restricted.

With the development of artificial intelligence (AI), deep learning models have been widely applied to text data processing. For example, the Chinese patent application CN 110750640 A discloses a text classification method based on a neural network model, including: acquiring text data, processing the text data; converting the preprocessed text data into text vectors; performing feature selection on the text vectors with a backpropagation (BP) neural network classification model, optimized based on a decision tree to obtain an initial text feature; training the BP neural network classification model with a stochastic gradient descent algorithm and a fine-tuning method according to the obtained initial text feature to obtain an optimal text feature; and classifying the text data with a classifier according to the optimal text feature, and outputting a classification result of the text data.

The Chinese patent application CN 109710763 A discloses a method for classifying text data, including: acquiring a text dataset; preprocessing the text to form a training dataset; constructing a deep neural network model; training the deep neural network model based on the training dataset; classifying and recognizing by using a trained deep neural network model.

The deep learning models have achieved the desirable effects for mining biomedical texts in recent years. However, the deep learning methods are implemented based upon huge training datasets; and due to the costly construction of large biomedical text training sets, the development of the deep learning in biomedical text mining is restricted. Therefore, existing manual collection mainly based on a pattern for the disease-associated databases fails to mine entity relations fully with the deep learning model and is heavily reliant on complex features of machine learning.

SUMMARY

An objective of the present disclosure is to provide an entity relation mining method based on a biomedical literature. The present disclosure can effectively recognize biomedical noun entities in the literature and mine potential relations between various entities.

To achieve the above-mentioned objective, the present disclosure uses the following technical solutions: An entity relation mining method based on a biomedical literature includes the following steps:
  (1) querying a disease-associated biomedical literature in a public database, and performing data preprocessing to obtain biomedical text data;
  (2) performing biomedical named entity recognition on obtained biomedical text data in combination with a regex matching pattern and a deep learning model; and
  (3) mining an entity relation with transfer learning and reinforcement learning based on an entity recognition result.

By acquiring the disease-associated biomedical literature from a network, extracting an abstract and a title and performing entity recognition and relation mining, the present disclosure can effectively recognize biomedical noun entities in the literature and mine potential relations between various entities.

The data preprocessing in step (1) may specifically include:
  acquiring abstract text data of the biomedical literature, filtering a website html tag and periodical information of the text data, and removing an overlong or overshort abstract; and performing a sentence tokenization on a text with a Stanford CoreNLP toolkit to finally obtain required high-quality biomedical text data.

Step (2) may specifically include:
  constructing an ncRNA entity word dictionary with a cross reference to an existing biomedical database, and designing the regex matching pattern to perform ncRNA entity recognition on the obtained biomedical text data; and
  constructing and training a bidirectional long short-term memory (LSTM)-conditional random field (CRF) neural network model to perform disease and gene entity recognition on the obtained biomedical text data.

The bidirectional LSTM-CRF neural network model may include an input layer, a bidirectional LSTM layer, a fully connected layer and a CRF layer, specifically:
  a first layer is the input layer, and each sentence is represented as a sequence composed of a vector, namely $X=(e_1, \ldots e_i, \ldots, e_n)$, to input to the model, where e is a distributed representation of each word, n is a length of the sentence, i is an ith word in the sentence, $e_1$ is a word vector of a first word, $e_i$ is a word vector of the ith word, and $e_n$ is a word vector of an nth word; on the bidirectional LSTM layer, forward and backward hidden vectors of each step are spliced to output to the fully connected layer, thereby obtaining a probability that each step corresponds to each tag; and a result from the fully connected layer is input to the CRF layer as an emission probability to decode an optimal tag sequence in all possible tag sequences.

The bidirectional LSTM-CRF neural network model may have a following input feature in the disease and gene entity recognition:

- a word feature, which is a word after word tokenization;
- a part-of-speech (POS) feature, which is multiple POSs tagged by a POS tagger;
- a character feature, including an uppercase, a lowercase and a spelling rule, and automatically learned through model training after random initialization of a model input end; and
- a chunk feature, which is a word combination.

The named entity recognition may be a supervised learning method, and an effective neural network model for the disease and gene named entity recognition may be trained with tagged data.

Step (3) may specifically include:

(3-1) integrating a disease-associated relation instance in a biomedical database as a tag dataset created by a non-standard task, and constructing, with an entity alignment method, an entity relation training dataset having a rich relational class, the entity relation training dataset including a gene-disease relational dataset and an ncRNA-disease relational database;

(3-2) performing a single-relation classification task with a single-relation pair extraction model, where the single-relation pair extraction model is based on a bidirectional encoder representations from transformers for biomedical text mining (BioBERT) model in a biomedical field and obtained by fine-tuning the BioBERT model with the entity relation training dataset;

(3-3) performing a multi-relation classification task with a multi-relation pair extraction model, the multi-relation pair extraction model using an encoder-decoder framework, and optimizing a triplet decoding sequence with assistant training of the reinforcement learning; and (3-4) mining an entity attribute from a disclosed disease, gene and ncRNA database, screening a triplet pair, integrating disease-gene relational data and disease-ncRNA relational data, and storing and querying data with a graph database Neo4j, where the triplet refers to a head entity, a tail entity and a relation between the head entity and the tail entity, namely (the head entity, the relation, and the tail entity), and in an actual application, the triplet is also referred to as triplet information.

In step (3-1), for a tagged entity that cannot be aligned during entity alignment, a synonym of the tagged entity may be obtained with an entity dictionary, and a synonym set may be used to match a word in a sentence.

In step (3-3), the optimizing a triplet decoding sequence with assistant training of the reinforcement learning may specifically include:

reading, by a decoder, a semantic vector generated by an encoder; generating, by the decoder, a relational class in response to generating each triplet, directly copying a first entity from a source statement with a copying mechanism to serve as a head entity, and copying a second entity from the source statement to serve as a tail entity, every three entities being output as one triplet; and generating, by the decoder, a relational class, a head entity and a tail entity of a next triplet, or ending decoding, where an entity involving in different triplets is repeatedly copied by the decoder.

Compared with the prior art, the present disclosure has the following beneficial effects:

1. The present disclosure automatically mines the relations between the biomedical entities from the biomedical text. With the tagged data for model training, the present disclosure can obtain an effective model for entity recognition, thereby automatically recognizing a large number of medical entities. While mining the entity relations, the present disclosure transfers the existing pre-trained model in the biomedical domain to the relation extraction task through the transfer learning, and optimizes pre-trained network parameters, thereby greatly shortening the model training time, reducing server resources for training, and achieving the desirable classification effect. For common relation overlaps in the biomedical text, the present disclosure processes the entity pair overlap and single entity overlap at the same time with an end-to-end model having a copying mechanism, and optimizes the triplet extraction sequence with the reinforcement learning in later training.

2. The disease-associated relation extraction task mainly focuses on the association with entity classes of the gene and the medicine. As a transcription product, the ncRNA is a biomolecule attracting more and more attention in the biomedical domain. The present disclosure first proposes the framework for mining the ncRNA-disease relation, automatically mines the disease-associated ncRNA from the literature, and carefully classifies the relation.

BRIEF DESCRIPTION OF THE DRAWINGS

The present disclosure will be further described below with reference to the accompanying drawings.

DETAILED DESCRIPTION OF THE EMBODIMENTS

The present disclosure is further described in detail below with reference to the accompanying drawings and embodiments. It is to be noted that the embodiments set forth hereinafter are for the ease of understanding, rather than limiting.

Figure 1:
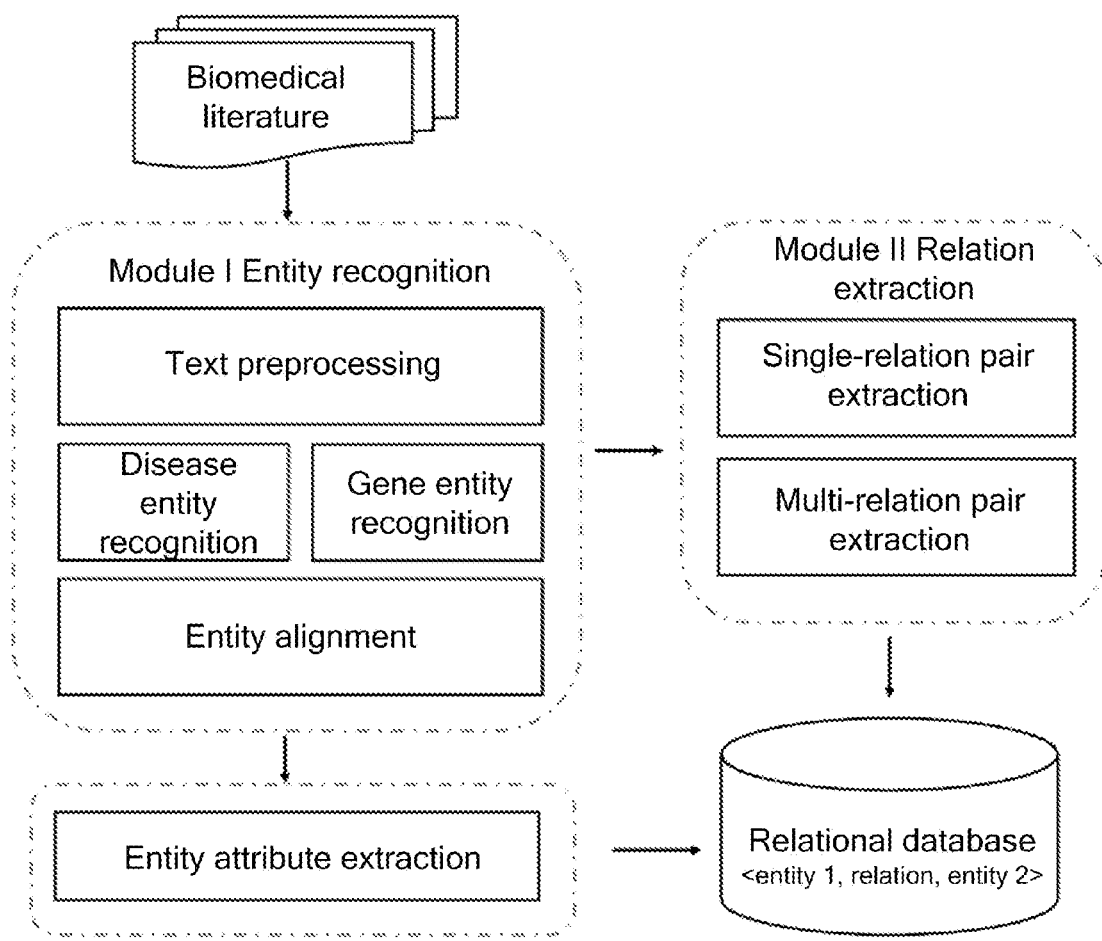
FIG. 1 is a flow chart of an entity relation mining method based on a biomedical literature according to the present disclosure.

As shown in FIG. 1, an entity relation mining method based on a biomedical literature includes: data acquisition of a biomedical literature, biomedical entity recognition, and entity relation mining.

A biomedical literature downloaded from a public database is preprocessed. Articles with classes matching with the appendix, corrigendum or recall are abandoned, and articles with overlong or overshort abstracts are also removed. Some articles are offered with excessive html tags, periodical information, and experimental registration information, and the redundant and ineffective information is deleted with a rule-based method. Title and abstract information of each literature are merged to serve as original unstructured text data.

There are sentence tokenization and word tokenization during standard preprocessing of most information extraction tasks. In the embodiment, Stanford CoreNLP, a natural language processing (NLP) tool compiled with Java, is used to perform the sentence tokenization and the word tokenization For English word tokenization, spaces and punctuations are usually used as points for tokenization.

The Stanford CoreNLP toolkit is used to perform the sentence tokenization on the text to obtain high-quality biomedical text data.

Biomedical named entity recognition is performed in combination with a regex matching pattern and a deep learning model, with the following specific steps:

An ncRNA entity word dictionary is constructed with a cross reference to an existing biomedical database, and an effective regex matching pattern is designed to perform ncRNA entity recognition.

Disease and gene entity recognition is performed on an extracted biomedical text through a feature of a bidirectional LSTM-CRF neural network model.

The bidirectional LSTM-CRF neural network model has a following input feature:
 a word feature, which is a word after word tokenization;
 a POS feature, which is multiple POSs tagged by a POS tagger;
 a character feature, including an uppercase, a lowercase and a spelling rule, and automatically learned through model training after random initialization of a model input end; and
 a chunk feature, which is a word combination.

Data in the named entity recognition is tagged with a BIO model, and an effective neural network model for the disease and gene named entity recognition is trained with tagged data.

Figure 2:
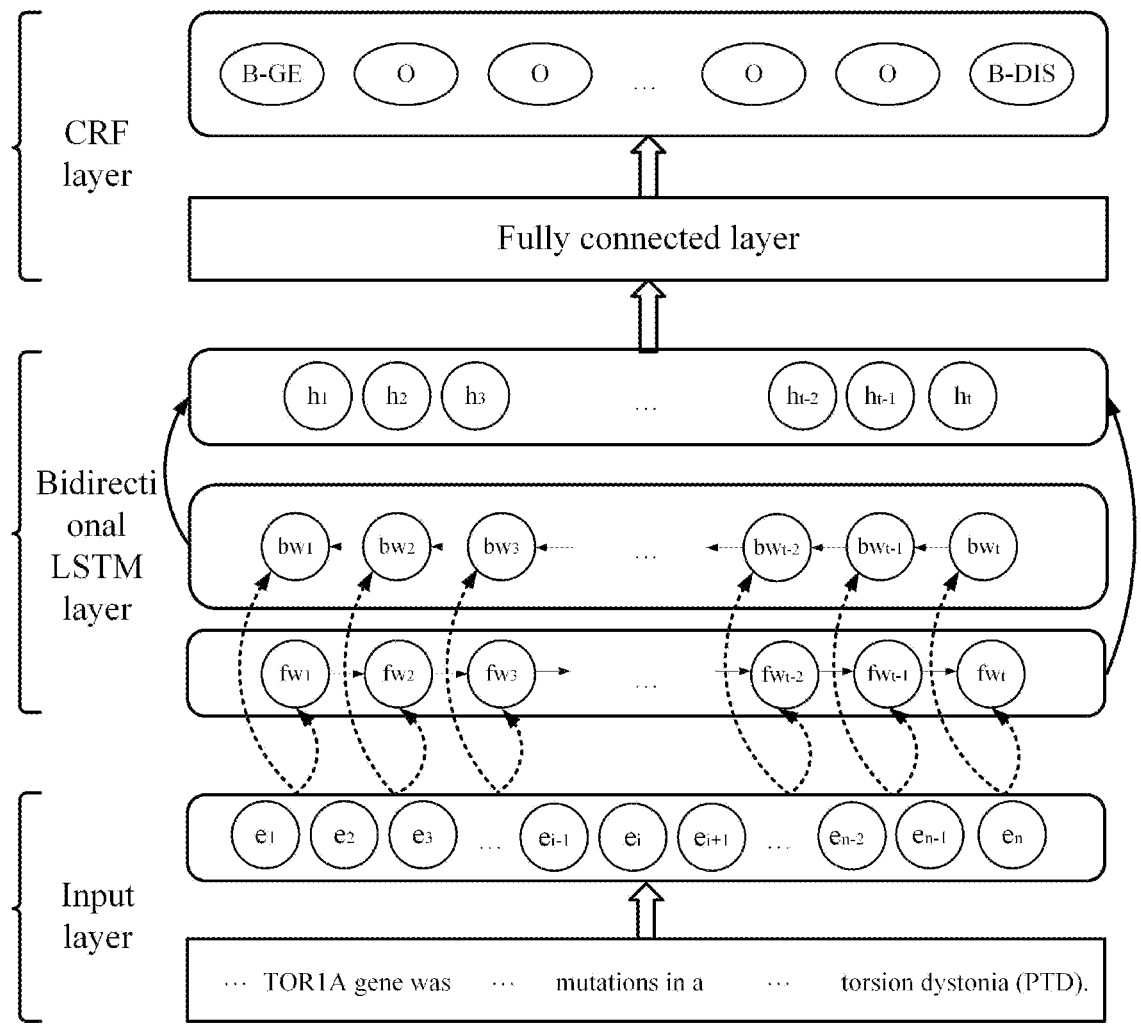
FIG. 2 is a schematic view of an overall framework of a bidirectional LSTM-CRF neural network model according to the present disclosure.

The model training is intended to output a tag of each word in a given sentence. The overall framework of the bidirectional LSTM-CRF neural network model is as shown in FIG. 2, specifically, a first layer is an input layer, and each sentence is represented as a sequence composed of a vector, namely $X=(e_1, \ldots e_i, \ldots, e_n)$, to input to the model, where e is a distributed representation of each word, and n is a length of the sentence. On a bidirectional LSTM layer, fw is a hidden state of the LSTM layer in forward propagation, while bw is a hidden state of the LSTM layer in backward propagation. Forward and backward hidden vectors of each step are spliced to obtain $H=(h_1, \ldots h_i, \ldots h_n)$, which is output to a fully connected layer having a size of [a dimension of a hidden layer, a number of tag classes] to obtain a probability that each step corresponds to each tag. A result from that layer is input to a CRF layer as an emission probability to decode an optimal tag sequence in all possible tag sequences. The model is used to maximize the log probability of the correct tag sequence during training, and predict the optimal tag path having the maximum score during decoding.

An entity relation is mined with transfer learning and reinforcement learning based on an entity recognition result, specifically:

A disease-associated relation instance from a biomedical database is integrated as a tag dataset created by a non-standard task, and a gene-disease relational dataset and an ncRNA-disease relational database having a rich relational class are constructed with an entity alignment method. For a tagged entity that cannot be aligned, a synonym of the tagged entity is obtained with an entity dictionary, and a synonym set is used to match a word in a sentence. The word matching with the synonym set is the tagged entity. The entity dictionary is constructed based on data integration of multiple databases.

Figure 3:
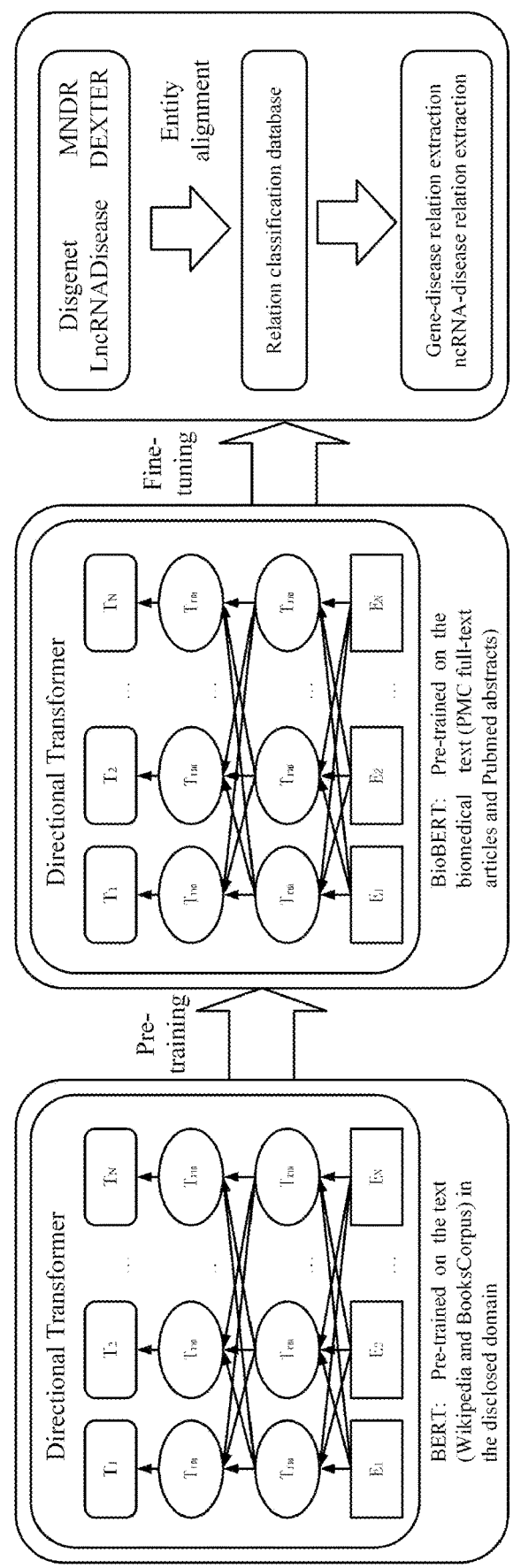
FIG. 3 is a schematic view of a single-relation pair extraction model according to the present disclosure.

The single-relation pair extraction task uses the transfer learning, as shown in FIG. 3. The bidirectional encoder representations from transformers (BERT) model is inapplicable to mining biomedical texts because it is trained on the dataset (news articles and Wikipedia) in the disclosed domain. Derived from the BERT, the BioBERT model is further trained on the biomedical text (PubMed Central (PMC) full-text articles and Pubmed abstracts) on the basis of pre-training of English Wikipedia data and book data. The biomedical pre-trained model is fine-tuned with the gene-disease relational dataset and the ncRNA-disease relational database to obtain a disease-associated biomedical relation extraction model. The relation classification dataset is constructed based on tag datasets created by other non-standard tasks. The gene-disease relations refer to the Disgenet database, and the ncRNA-disease relations refer to three databases, namely LncRNADisease, MNDR and DEXTER. With synonym dictionaries in gene and disease corpora, the tagged entity is aligned to the word in the instance to construct the gene-disease relational dataset and the ncRNA-disease relational database having the rich relational class.

Figure 4:
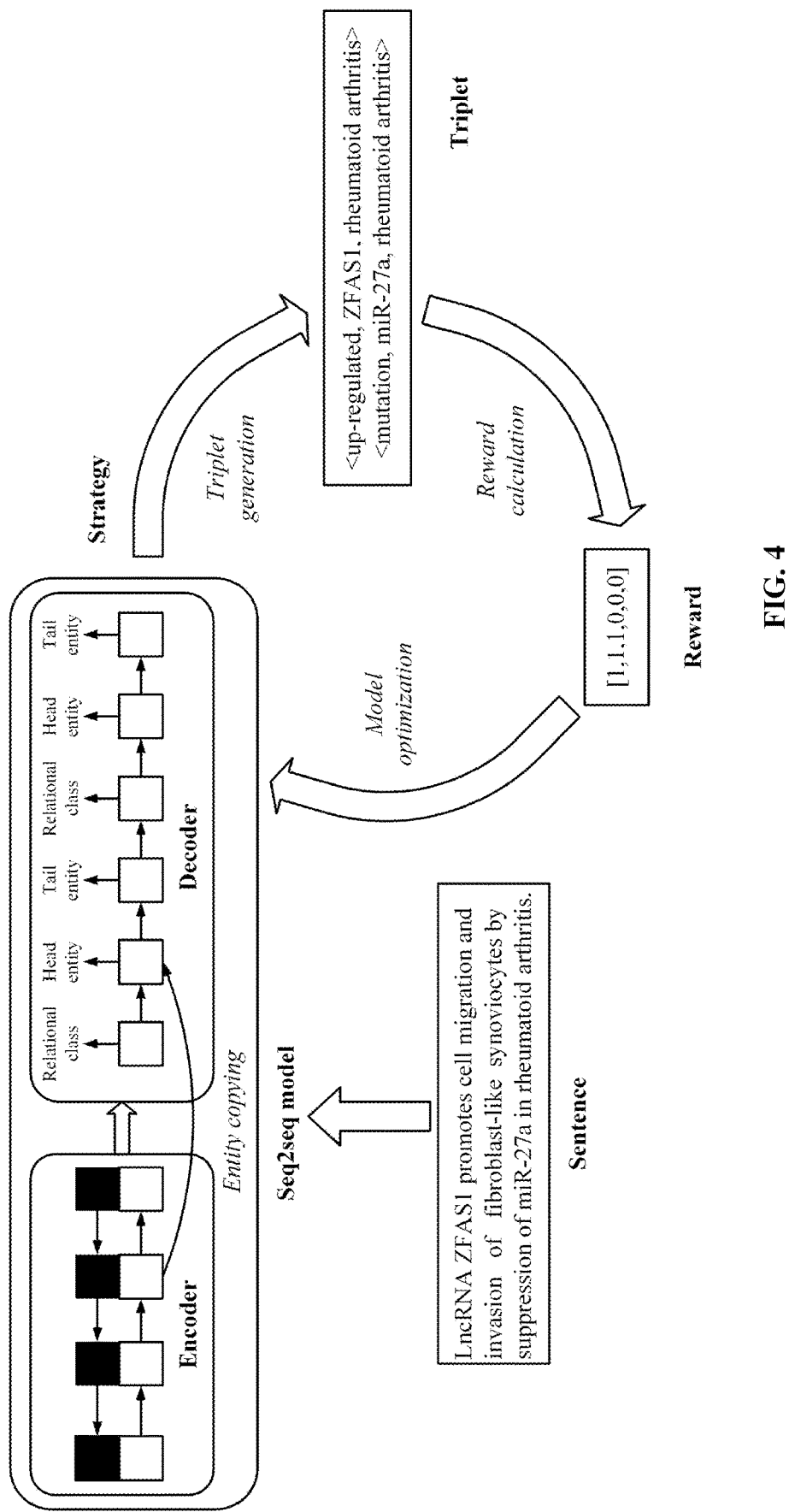
FIG. 4 is a schematic view of a multi-relation pair extraction model according to the present disclosure.

The multi-relation pair extraction model is as shown in FIG. 4. The BERT model fine-tuned on the biomedical text is used to generate a word vector to input to a gated recurrent unit (GRU) of the encoder. A decoder reads a semantic vector generated by the encoder to directly generate a triplet. In response to generating each triplet, the decoder generates a relational class, directly copies a first entity from a source statement with a copying mechanism to serve as a head entity, and copies a second entity from the source statement to serve as a tail entity. By the same reasoning, the decoder can extract multiple triplets. An entity involving in different triplets can be repeatedly copied by the decoder.

As a strategy in the reinforcement learning, the relation extraction model is used to generate triplet data, with actions generated in each time step. It is assumed by the model that a better extraction sequence can generate more effective triplets. The reward is related to the generated triplets; and the more the generated correct triplets, the higher the reward. The reinforcement learning feeds the obtained reward back to the relation extraction model to update parameters for strategy optimization, thereby forming a learning loop.

Gene and disease information in HUGO Gene Nomenclature Committee (HGNC) and comparative toxicogenomics database (CTD) databases are directly downloaded or acquired through a crawler technology to serve as attributes. Attributes of the genes include names, identity (ID) numbers in National Center of Biotechnology Information (NCBI) GENE, classes, position information on chromosomes, sequence information, alias names, family classes and ID numbers in other databases, etc. Attributes of the diseases include names, ID numbers in MEDIC, definitions, alias names, parent classes in the classification systems, and ID numbers (MESH and DO) in other databases, etc. The ncRNA entity mainly refers to information in mirBase, LNCipedia and circBase databases. The graph database Neo4j is used as a database for storing disease-gene/ncRNA associated information.

By applying the present disclosure to more than 60,000 biomedical literatures, there are more than 150,000 disease-gene relation pairs and more than 110,000 disease-ncRNA relation pairs, and includes nearly 20,000 disease entities, 16,000 gene entities and 12,000 ncRNA entities; and therefore, the present disclosure effectively mines the potential relations between various entities.

The above embodiments are provided merely for an objective of describing the present disclosure and are not intended to limit the scope of the present disclosure. The scope of the present disclosure is defined by the appended claims. Various equivalent replacements and modifications made without departing from the spirit and scope of the present disclosure should all fall within the scope of the present disclosure.

What is claimed is:

1. An entity relation mining method based on a biomedical literature, comprising the following steps:
    querying a disease-associated biomedical literature in a public database, and performing data preprocessing to obtain biomedical text data;
    performing biomedical named entity recognition on obtained biomedical text data in combination with a regex matching pattern and a deep learning model; and
    mining an entity relation with transfer learning and reinforcement learning based on an entity recognition result, comprising:
        integrating a disease-associated relation instance in a biomedical database as a tag dataset created by a non-standard task, and constructing, with an entity alignment method, an entity relation training dataset having a rich relational class, the entity relation training dataset comprising a gene-disease relational dataset and an ncRNA-disease relational database;
        performing a single-relation classification task with a single-relation pair extraction model, wherein the single-relation pair extraction model is based on a bidirectional encoder representations from transformers for biomedical text mining (BioBERT) model in a biomedical domain and obtained by fine-tuning the BioBERT model with the entity relation training dataset;
        performing a multi-relation classification task with a multi-relation pair extraction model, the multi-relation pair extraction model using an encoder-decoder framework, and optimizing a triplet decoding sequence with assistant training of the reinforcement learning; and
        mining an entity attribute from a disclosed disease, gene and ncRNA database, screening a triplet pair, integrating disease-gene relational data and disease-ncRNA relational data, and storing and querying data with a graph database.

2. The entity relation mining method based on a biomedical literature according to claim 1, wherein the data preprocessing specifically comprises:
    acquiring abstract text data of the biomedical literature, filtering a website html tag and periodical information of the text data, and removing an overlong or overshort abstract; and performing a sentence tokenization on a text with a Stanford CoreNLP toolkit to finally obtain required biomedical text data.

3. The entity relation mining method based on a biomedical literature according to claim 1, wherein the performing biomedical named entity recognition on obtained biomedical text data in combination with a regex matching pattern and a deep learning model specifically comprises:
    constructing a non-coding ribonucleic acid (ncRNA) entity word dictionary with a cross reference to an existing biomedical database, and designing the regex matching pattern to perform ncRNA entity recognition on the obtained biomedical text data; and
    constructing and training a bidirectional long short-term memory (LSTM)-conditional random field (CRF) neural network model to perform disease and gene entity recognition on the obtained biomedical text data.

4. The entity relation mining method based on a biomedical literature according to claim 3, wherein the bidirectional LSTM-CRF neural network model comprises an input layer, a bidirectional LSTM layer, a fully connected layer and a CRF layer, specifically:
    a first layer is the input layer, and each sentence is represented as a sequence composed of a vector, namely $X=(e_1, \ldots e_i, \ldots, e_n)$, to input to the model, wherein e is a distributed representation of each word, n is a length of the sentence, i is an $i^{th}$ word in the sentence, $e_1$ is a word vector of a first word, $e_i$ is a word vector of the $i^{th}$ word, and $e_n$ is a word vector of an nth word; on the bidirectional LSTM layer, forward and backward hidden vectors of each step are spliced to output to the fully connected layer, thereby obtaining a probability that each step corresponds to each tag; and a result from the fully connected layer is input to the CRF layer as an emission probability to decode an optimal tag sequence in all tag sequences.

5. The entity relation mining method based on a biomedical literature according to claim 3, wherein the bidirectional LSTM-CRF neural network model has a following input feature in the disease and gene entity recognition:
    a word feature, which is a word after word tokenization;
    a part-of-speech (POS) feature, which is multiple POSs tagged by a POS tagger;
    a character feature, comprising an uppercase, a lowercase and a spelling rule, and automatically learned through model training after random initialization of a model input end; and
    a chunk feature, which is a word combination.

6. The entity relation mining method based on a biomedical literature according to claim 1, wherein in the integrating a disease-associated relation instance in a biomedical database as a tag dataset created by a non-standard task, and constructing, with an entity alignment method, an entity relation training dataset having a rich relational class, for a tagged entity that is not aligned during entity alignment, a synonym of the tagged entity is obtained with an entity dictionary, and a synonym set is used to match a word in a sentence.

7. The entity relation mining method based on a biomedical literature according to claim 1, wherein the optimizing a triplet decoding sequence with assistant training of the reinforcement learning specifically comprises:
    reading, by a decoder, a semantic vector generated by an encoder; generating, by the decoder, a relational class in response to generating each triplet, directly copying a first entity from a source statement with a copying mechanism to serve as a head entity, and copying a second entity from the source statement to serve as a tail entity, every three entities being output as one triplet; and generating, by the decoder, a relational class, a head entity and a tail entity of a next triplet, or ending decoding.

* * * * *